(12) United States Patent
Laimer et al.

(10) Patent No.: US 11,033,373 B2
(45) Date of Patent: Jun. 15, 2021

(54) INTRAORAL SUCTIONING DEVICE FOR INTRAORAL NEGATIVE PRESSURE WOUND TREATMENT AND METHOD FOR MANUFACTURING THE INTRAORAL SUCTIONING DEVICE

(71) Applicant: Medizinische Universität Innsbruck, Innsbruck (AT)

(72) Inventors: Johannes Laimer, Dort Tirol (IT); Emanuel Bruckmoser, Innsbruck (AT)

(73) Assignee: MEDIZINISCHE UNIVERSITÄT INNSBRUCK, Innsbruck (AT)

(*) Notice: Subject to any disclaimer, the term of this patent is extended or adjusted under 35 U.S.C. 154(b) by 0 days.

(21) Appl. No.: 16/463,175

(22) PCT Filed: Nov. 21, 2017

(86) PCT No.: PCT/EP2017/079908
§ 371 (c)(1),
(2) Date: May 22, 2019

(87) PCT Pub. No.: WO2018/095904
PCT Pub. Date: May 31, 2018

(65) Prior Publication Data
US 2019/0374322 A1 Dec. 12, 2019

(30) Foreign Application Priority Data

Nov. 23, 2016 (EP) .................... 16200331

(51) Int. Cl.
*A61C 19/06* (2006.01)
*A61M 1/00* (2006.01)
(Continued)

(52) U.S. Cl.
CPC .......... *A61C 19/06* (2013.01); *A61C 17/0208* (2013.01); *A61M 1/0088* (2013.01);
(Continued)

(58) Field of Classification Search
CPC ....... A61C 19/06; A61C 19/063; A61C 17/08; A61C 17/0208; A61C 17/0211;
(Continued)

(56) References Cited

U.S. PATENT DOCUMENTS 3,489,141 A * 1/1970 Warren, Jr. ........ A61C 17/0211
601/164
3,731,675 A * 5/1973 Kelly ................. A61C 17/0211
601/164
(Continued)

FOREIGN PATENT DOCUMENTS

CN 201510550 * 6/2010
CN 103751863 * 9/2010
(Continued)

OTHER PUBLICATIONS

Office Action (Communication) dated Jul. 30, 2019, by the European Patent Office in corresponding European Patent Application No. 16 200 331.3. (6 pages).
(Continued)

*Primary Examiner* — Edward Moran
*Assistant Examiner* — Matthew P Saunders
(74) *Attorney, Agent, or Firm* — Buchanan Ingersoll & Rooney PC

(57) ABSTRACT

The present disclosure relates to an intraoral suctioning device for intraoral negative pressure wound treatment and a method for manufacturing the same. In order to permanently maintain the negative pressure in a wound with a view to an improved wound treatment and regeneration process, the intraoral suctioning device for the intraoral negative pressure wound treatment as disclosed can include a dental splint, an elastic membrane sealing an aperture formed in the dental splint so as to define a sealed wound treatment area on the inside of the dental splint, and a
(Continued)

suctioning channel system for evacuating the wound treatment area.

16 Claims, 2 Drawing Sheets

(51) Int. Cl.
    *A61C 17/02*     (2006.01)
    *A61C 17/08*     (2006.01)

(52) U.S. Cl.
    CPC ............ *A61C 17/08* (2019.05); *A61M 1/0084* (2013.01); *A61M 2210/0625* (2013.01)

(58) Field of Classification Search
    CPC ..... A61C 17/043; A61C 17/036; A61C 17/04; A61C 17/06; A61M 1/008; A61M 1/009; A61M 1/0088; A61M 1/0084; A61M 1/00; A61M 2210/0625
    USPC .......................................................... 433/93
    See application file for complete search history.

(56) References Cited

U.S. PATENT DOCUMENTS

| | | | | |
|---|---|---|---|---|
| 6,314,960 B1* | 11/2001 | Vines | ................... | A61C 19/063 128/859 |
| 6,406,447 B1* | 6/2002 | Thrash | ............... | A61C 17/0211 601/159 |
| 6,471,685 B1* | 10/2002 | Johnson | .............. | A61F 13/0246 604/890.1 |
| 9,855,123 B2* | 1/2018 | Wolgin | ................. | A61M 1/009 |
| 2011/0282309 A1* | 11/2011 | Adie | ................... | A61F 13/0209 604/319 |
| 2012/0116334 A1* | 5/2012 | Albert | ................. | A61F 13/0216 604/319 |
| 2013/0019374 A1* | 1/2013 | Schwartz | ................ | A61F 13/102/69 |
| 2013/0310780 A1* | 11/2013 | Phillips | ............... | A61L 26/0095 604/319 |
| 2013/0310781 A1* | 11/2013 | Phillips | ................... | C08L 83/04 604/319 |
| 2015/0159066 A1* | 6/2015 | Hartwell | ............... | A61L 15/225 604/319 |
| 2015/0216732 A1* | 8/2015 | Hartwell | ........... | A61F 13/00021 604/319 |
| 2016/0000544 A1* | 1/2016 | Alexander | ........... | A61C 19/063 601/11 |
| 2016/0067022 A1* | 3/2016 | Jetton | ................... | A61H 9/0057 433/92 |
| 2016/0120706 A1* | 5/2016 | Collinson | ............... | A61L 15/58 604/319 |
| 2016/0144084 A1* | 5/2016 | Collinson | ........... | A61M 1/0088 604/319 |
| 2017/0165040 A1* | 6/2017 | Wolgin | ................. | A61C 17/08 |
| 2018/0104034 A1* | 4/2018 | Wolgin | ................ | A61M 1/009 |
| 2020/0023104 A1* | 1/2020 | Eriksson | ........... | A61F 13/00068 |

FOREIGN PATENT DOCUMENTS

| | | | | |
|---|---|---|---|---|
| CN | 101822853 | * | 4/2014 | |
| CN | 204951757 U | | 1/2016 | |
| CN | 205459177 U | | 8/2016 | |
| DE | 102014015163 A1 | * | 4/2016 | ............ A61C 19/06 |
| DE | 102014015163 A1 | | 4/2016 | |
| RU | 156501 U1 | | 11/2015 | |
| WO | 2012069794 A1 | | 5/2012 | |

OTHER PUBLICATIONS

D. Halama, et al., "Intraoral Application of Vacuum-Assisted Closure in the Treatment of an Extended Mandibular Keratocyst", Zentralbl Chir, 2004, pp. S53-S56, vol. 129.

International Search Report (PCT/ISA/210) and Written Opinion (PCT/ISA/237) dated Feb. 14, 2018, by the European Patent Office as the International Searching Authority for International Application No. PCT/EP2017/079908.

Orgill, et al., "Negative pressure wound therapy: past, present and future", International Wound Journal, 2013, pp. 15-19, ISSN1742-4801.

\* cited by examiner

INTRAORAL SUCTIONING DEVICE FOR INTRAORAL NEGATIVE PRESSURE WOUND TREATMENT AND METHOD FOR MANUFACTURING THE INTRAORAL SUCTIONING DEVICE

The present invention relates to an intraoral suctioning device for intraoral negative pressure wound treatment and a method for manufacturing the intraoral suctioning device.

Complex wounds of the soft tissue covering the jawbones on the basis of bone necrosis ("dead" bone) may occur as a side effect from medication, in particular after intravenous application of bisphosphonates or the monoclonal antibody Denosumab. These drugs are used in particular for the treatment of malign cancer or osteoporosis. One generally refers to this type of bone necrosis as medication-related osteonecrosis of the jaw (MRONJ), in particular to bisphosphonate-related osteonecrosis of the jaw (BRONJ) if the necrosis is triggered by medication of bisphosphonates. That is, BRONJ is a sub-term of MRONJ, which covers all kinds of medication-related necroses in the area of the jawbones. MRONJ/BRONJ occurs as a side effect roughly in 1 to 2% of all cancer patients treated with bisphosphonates or Denosumab. A particularly challenging intraoral condition is that MRONJ/BRONJ not only affects the jawbone but also the intraoral mucosal tissue.

Apart from MRONJ/BRONJ also radiotherapy of head and neck cancers can affect jaw bone vitality and lead to osteoradionecrosis (ORN) of the jaw ("dead" bone). As with MRONJ/BRONJ the intraoral soft tissue, i.e. the gingiva and/or intraoral mucosa can be affected.

After major tumor surgery of the head and neck region, the resulting tissue defects often need covering by free flaps to replace resected tissues. In order to ensure adequate blood supply, free flaps require connection to vessels of the head and neck region (microvascular anastomoses of arteries and veins). Many factors are known to compromise the vitality of such a free flap which can lead to partial or full necrosis of the flap resulting in complex intraoral wound situations.

Finally, after operations in the oral cavity wounds can open up again which is referred to as wound dehiscence. Especially in hygienically compromised situations (e.g. in patients on intensive care units after major trauma surgery) management of these wounds is often complex. Also, loss of tissue (e.g. due to trauma) can compromise wound closure and result in challenging conditions that are hard to handle.

The current state of the art therapy for osteonecrosis in the area of the jawbones includes medication (e.g. mouth rinse and/or antibiotics) as well as surgical procedures. Current therapies suffer from high failure and relapse rates, respectively, or are associated with surgeries which are extremely stressful and time-consuming for the patient. At present, there is no generally renowned, minimally invasive intraoral wound treatment method available which offers a high likelihood of success. The same is true for osteoradionecrosis of the jaw as the clinical features of this condition are very similar to the characteristics of MRONJ/BRONJ. In cases of free flap necrosis the necrotic tissue has to be surgically removed and—in the worst case—another free flap has to be harvested to recover the tissue defect. Finally, intraoral wound dehiscence often requires further surgery which could potentially be avoided through application of negative pressure for proper intraoral wound therapy.

Since about two decades, negative pressure wound therapy (NPWT) has been widely used for the management of complex wounds and tissue defects on the external body surface.

According to the Review Article "Negative pressure wound therapy: past, present and future" by Dennis P. Orgill and Lauren R. Bayer, International Wound Journal 2013; 10 (suppl. 1): 15-19, ISSN1742-4801, the negative pressure wound therapy (NPWT) creates a closed, moist wound environment while applying sub-atmospheric pressure that removes exudate. There are four primary NPWT mechanisms of action, namely macrodeformation, microdeformation, fluid removal and environmental control of the wound, wherein multiple secondary actions through cell signaling effects occur as a result of the interaction of the primary mechanisms of action.

The Article "Intraoral Application of Vacuum-Assisted Closure in the Treatment of an Extended Mandibular Keratocyst" by D. Halama, A. Hemperich and D. Frerich of the Universitätsklinikum Leipzig, Zentralbl Chir 2014; 129: S53-S56, J. A. Barth Verlag in Georg Thieme Verlag K G, DOI 10.1055/s-2004-822669, ISSN 0044-409X describes an intraoral suctioning device for the intraoral negative pressure treatment of a "keratocyst" which is an odontogenic tumor that appears as an intraosseous cavity (the boundaries of which are lined by two distinct layers of epithelial and fibrous tissue). The device comprises a suctioning tube that is connectable to a suctioning pump for evacuating the intraosseous cavity, a highly elastic silicone body formed by injection-molding around the end of the suctioning tube for sealing the outer borders of the cavity, and a soft-foam PVA-sponge for filling the cavity. The silicone body is directly attached to the suctioning tube and basically forms an obturator plug for permanently closing the wound during negative pressure wound treatment.

It has to be emphasized that the herein mentioned publication does not refer to the use of negative pressure for proper intraoral wound treatment. The aim of the above described mode of negative pressure application was intended to reduce the intraosseous cavity (corresponding to the keratocyst) in size and volume. Also, no technique to press the foam against the gingiva and/or mucosa is described, although this would be crucial for proper negative pressure wound treatment with regard to positive effects such as macro- and microdeformation.

The document CN205459177 U discloses an intraoral suctioning device for the treatment of tooth-borne infectious and non-infectious diseases (such as pulpitis, apical periodontitis, periapical abscess, periapical cyst, etc.). The device is configured to be attached to the teeth by means of adhesive, wherein a suction drainage applies negative pressure in order to remove infectious dental soft tissue and/or stimulate bone regeneration, however, the application does not refer to the use of negative pressure for proper intraoral wound treatment.

The object of the present invention is to provide an improved intraoral suctioning device for the negative pressure treatment that is capable of permanently maintaining the negative pressure in the wound area with a view to an improved wound treatment and regeneration process.

The object is solved by the subject matter of the independent claims.

The intraoral suctioning device for the intraoral negative pressure wound treatment according to the present invention as claimed in claim 1 comprises a dental splint, an elastic membrane sealing an aperture formed in the dental splint so as to define a wound treatment area at the inside of the dental splint, and a suctioning channel system for evacuating the wound treatment area. The intraoral suctioning device may comprise an additional suctioning channel system perforating through a lining of the dental splint so as to be located in the sections outside the wound treatment area. This is to gain additional down force on the dental splint to be pressed onto the soft tissue covering the jaw bone preventing the device from being lifted off. This technical feature may require a second vacuum pump or at least a separate pressure control to be provided by a single pump. Furthermore, a purging channel system can be integrated into the splint to enable irrigation of the wound area with antibacterial or antiseptic solutions. The device is preferably configured to sealingly fit to an upper or lower jaw of a patient, wherein the dental splint serves as a rigid carrier structure or backbone for securing a firm fit on the patient's jaw for permanently maintaining the device and its components in the predetermined intraoral position. Unlike the silicone plug of the conventional device, the elastic membrane seals the wound and presses the foam onto to the wound area without directly interacting with the wound, which further improves the wound treatment and regeneration process. Therefore, the intraoral suctioning device according to the present invention is capable of permanently maintaining the negative pressure in the wound treatment area, so as to improve the wound treatment and regeneration process.

Preferable embodiments are claimed in the sub-claims.

Terms and Definitions

The term aperture refers to a portion provided in the dental splint, wherein material is preferably removed from the shape of the dental splint adapted to the patient's jaw. The aperture is preferably provided in the area of the intraoral wound of the patient to be treated by negative pressure treatment. The dental splint may comprise one or more apertures, in particular two or three apertures. Each aperture may be sealed by its own elastic membrane. Alternatively, several apertures may be sealed by one common elastic membrane. The aperture may be embodied as a cavity, recess, opening, through-hole, cutout portion and the like.

The inside of the device and/or dental splint shall be the side that is configured to be sealingly fitted to the patient's jaw. The outside of the device and/or dental splint shall be the side facing away from the jaw of the patient to which the device is sealingly fitted. In operation, the inside of the device and/or dental splint is configured to be the negative pressure side and the outside of the device and/or dental splint is configured to be the positive pressure side.

The term suction channel system applies to any system allowing fluid removal from the wound treatment area. The term purging channel system applies to any system allowing fluid supply to the wound treatment area. Each wound treatment area may comprise its own purging channel system and/or its own suctioning channel system. Alternatively, separate wound treatment areas may share one common purging channel system and/or one common suctioning channel system.

According to a preferred embodiment of the invention, the dental splint comprises at least one of the following features:

The device and/or dental splint is configured to sealingly fit to a patient's jaw.

The dental splint is formed from plastic material, preferably from thermoplastic polyurethane (TPU) and/or polycarbonate (PC). In case of manufacturing the intraoral device by 3D-printing technology, the dental splint can be fabricated by any printable material.

The dental splint comprises at least one layer, preferably at least two layers made from different materials, more preferably an outer layer from a harder material and an inner layer from a softer material.

The dental splint is formed from DURASOFT® (commercially available from SCHEU-DENTAL GmbH; www.scheu-dental.com), or any printable material in case of manufacturing the intraoral device by 3D-printing technology.

The dental splint is formed from a material approved and/or admitted for clinical purposes by the Bundesinstitut für Risikobewertung (BfR) and/or the Food and Drug Administration (FDA).

The dental splint is formed from a material certified according to ISO 10993 and/or EN ISO 7405.

The dental splint is formed from an air-impermeable material.

The dental splint is made from a plate having a thickness in a range from 1.0 to 5.0 mm, preferably 1.2 to 2.5 mm, more preferably 1.2 mm (0.7 mm first layer, 0.5 mm second layer), 1.8 mm (0.8 mm first layer, 1.0 mm second layer) or 2.5 mm (1.2 mm first layer, 1.3 mm second layer).

The dental splint is individually adapted to a patient's jaw, preferably individually adapted to a cast model of a patient's jaw.

The dental splint is formed by 3-D printing, preferably on the basis of a 3-D-scan.

The dental splint is formed by deep-drawing and/or pressure-molding.

The dental splint is formed under vacuum conditions.

The dental splint is approximately arc-shaped or semicircular as seen in top view.

The dental splint is configured to partially or fully cover tooth quadrant 1 (right) and/or tooth quadrant 2 (left) of the upper jaw, or tooth quadrant 3 (left) and/or tooth quadrant 4 (right) of the lower jaw according to the FDI tooth scheme (ISO 3950 notation).

The dental splint is configured to partially or fully cover a portion corresponding to at least one tooth, preferably two or more teeth, more preferably two or more consecutive teeth, out of teeth 11 to 18 (11, 12, 13, 14, 15, 16, 17, 18) and/or teeth 21 to 28 (21, 22, 23, 24, 25, 26, 27, 28) of the upper jaw, or teeth 31 to 38 (31, 32, 33, 34, 35, 36, 37, 38) and/or teeth 41 to 48 (41, 42, 43, 44, 45, 46, 47, 48) of the lower jaw according to the FDI tooth scheme (ISO 3950 notation).

The inside of the dental splint is concavely-shaped (e.g. in cross-section, preferably along at least a part or the entire (arc) length of the dental splint).

The outside of the dental splint is convexly-shaped (e.g. in cross-section, preferably along at least a part or the entire (arc) length of the dental splint).

According to another preferred embodiment of the invention, the elastic membrane comprises at least one of the following features:

The elastic membrane is attached to the dental splint.

The elastic membrane is part of the dental splint.

The elastic membrane fully covers the aperture.

The elastic membrane is adapted to the shape of the aperture.

The elastic membrane air-tightly seals the aperture.

The elastic membrane is formed from an autopolymerizing and/or cold-curing and/or A-silicone-based and/or permanently soft relining material.

The elastic membrane is formed from an air-impermeable material.

The outside of the elastic membrane is flush with the outside of the dental splint, preferably along a part of or along the entire circumference of the elastic membrane.

The elastic membrane has a thickness in a range from 0.1 to 5.0 mm, preferably 0.5 to 4.0 mm, more preferably 1.0 to 3.0 mm.

The elastic membrane is elastically deformable upon evacuation of the wound treatment area due to a pressure difference occurring on both sides of the elastic membrane, so that the elastic membrane enters into the aperture. The outside of the elastic membrane is preferably exposed to ambient pressure.

The elastic membrane is formed from Ufi Gel®, preferably Ufi Gel® SC (commercially available from VOCO GmbH, Cuxhaven, Germany; www.voco.com/en). In case of manufacturing the intraoral device by means of 3D-printing technology, the elastic membrane consists of one or more printable compounds providing the required elasticity and durability.

The elastic membrane is formed separately from the dental splint and subsequently attached to the dental splint after curing. In case of manufacturing the intraoral device by means of 3D-printing technology, the elastic membrane is printed as integral part of the whole device.

The elastic membrane is formed as a patch.

The elastic membrane is attached to the dental splint by means of adhesive, preferably adhesive liquid.

The elastic membrane is formed as an integral part of the dental splint, preferably by 3D-printing technology.

The membrane comprises a suctioning and/or a purging channel system.

According to yet another preferred embodiment of the invention, the aperture comprises at least one of the following features:

The aperture is provided in a portion of the dental splint corresponding to tooth quadrant 1 (right) and/or tooth quadrant 2 (left) of the upper jaw, or tooth quadrant 3 (left) and/or tooth quadrant 4 (right) of the lower jaw according to the FDI tooth scheme (ISO 3950 notation).

The aperture is provided in a portion of the dental splint corresponding to at least one tooth, preferably two or more teeth, more preferably two or more consecutive teeth, out of teeth 11 to 18 (11, 12, 13, 14, 15, 16, 17, 18) and/or teeth 21 to 28 (21, 22, 23, 24, 25, 26, 27, 28) of the upper jaw, or teeth 31 to 38 (31, 32, 33, 34, 35, 36, 37, 38) and/or teeth 41 to 48 (41, 42, 43, 44, 45, 46, 47, 48) of the lower jaw according to the FDI tooth scheme (ISO 3950 notation).

The aperture is circularly-shaped or oval-shaped as seen in a top view. Preferably, the aperture is shaped according to the contour of the wound area.

The aperture is embodied as a cavity, recess, opening, through-hole or cutout portion. The aperture is preferably formed as a through hole extending from the inside to the outside of the dental splint, preferably along a linear axis.

The aperture is formed by material removal from the dental splint, preferably by material removal from the shape of the dental splint that is adapted to the patient's jaw. In case of a 3D-printed device the aperture is designed on the computer prior to be printed in form of an elastic membrane which defines the aperture underneath.

The aperture is closed by an obturator plug to be removed from and/or to the inside of the dental splint prior to the relining of the splint should this be required to ensure sufficient seal for maintenance of adequate negative pressure, wherein the obturator plug is preferably fixed in position and/or partially or fully covered by a lining of the dental splint at the inner side thereof. This is to protect both the suctioning and the purging channel system from clogging during the relining procedure.

The aperture is located at the apex and/or on at least one of the flanks of the dental splint as seen in cross-section.

According to yet another preferred embodiment of the invention, the wound treatment area comprises at least one of the following features:

The wound treatment area is air-tightly sealed when the device is fitted to the patient's jaw.

The wound treatment area is located between and/or defined by the elastic membrane and portions of the inner and outer arc of the dental splint adjacent to the aperture.

The wound treatment area comprises a wound on the patient's jawbone when the device is fitted to the patient's jaw, particularly a wound resulting from medication-related osteonecrosis of the jaw (MRONJ), more particularly a wound resulting from bisphosphonate-related osteonecrosis of the jaw (BRONJ), or particularly from osteoradionecrosis (ORN), or particularly from free flap necrosis, or particularly from wound dehiscence, or a wound, which is prophylactically treated to prevent wound dehiscence.

The wound treatment area is configured to be evacuated by suctioning air through the suctioning channel system when the device is fitted to the patient's jaw.

The wound treatment area is partially or fully filled with a porous elastic material, preferably a foam-type and/or sponge-type and/or open-pore material, wherein the porous elastic material is preferably configured to be compressed onto the wound by the elastic membrane upon evacuation of the wound treatment area when the device is fitted to the patient's jaw. The wound treatment area is preferably entirely filled with one single piece of the porous elastic material. The porous elastic material may be a polyurethane foam, e.g. with a pore size of 400 to 600 µm, or a polyvinyl alcohol foam, e.g. with a pore size of 60 to 270 µm.

According to yet another preferred embodiment of the invention, the suctioning channel system comprises at least one of the following features:

The suctioning channel system allows removing fluid from the wound treatment by suction, preferably to the outside of the dental splint.

The suctioning channel system is partially or fully provided in the dental splint.

The suctioning channel system comprises an inlet. The inlet may comprise at least one of the following features:

The inlet opens to the aperture and/or the wound treatment area.

The inlet is located inside the dental splint and/or provided on the inside of the dental splint and/or is partially or fully defined by the material of the dental splint.

The inlet has at least one orifice. The orifice may diverge from an upstream side towards a downstream side thereof. The orifice may be adjacent to the aperture and/or an axis of the orifice may be aligned with a center of the aperture and/or a center of the wound treatment area. At least one orifice may be provided at a position remote from the aperture in order to increase the area to be evacuated at the inside of the dental splint so as to increase the down force on the splint.

A plurality of orifices may be arranged along and/or around the aperture, preferably equally spaced, more preferably along a part or the entire circumference of the aperture.

The inlet is located between the elastic membrane and a lining.

The suctioning channel system comprises an outlet. The outlet may be located outside the dental splint and/or provided on the outside of the dental splint and/or be partially or fully defined by the material of the dental splint. The outlet may be connectable to a suctioning pump.

The suctioning channel system comprises at least one suctioning channel. The suctioning channel preferably comprises at least one of the following features:
 The suctioning channel connects the inlet and the outlet of the suctioning channel system.
 The suctioning channel has at least one linear portion.
 The suctioning channel has at least one branched portion.
 The suctioning channel has at least one circular portion.
 The suctioning channel partially or fully extends within the dental splint and/or is at least partially or fully formed and/or defined by the material of the dental splint.
 The suctioning channel has a diameter in a range from 0.1 to 5 mm, preferably in a range from 0.5 to 4 mm, more preferably in a range from 1 to 3 mm.

The suctioning channel system comprises at least one tube. The tube may be embedded in the dental splint and/or the elastic membrane and/or the lining. The tube may penetrate the dental splint and/or the elastic membrane and/or the lining. The tube may extend beyond the inside and/or beyond the outside of the dental splint. The tube may partially or fully form and/or define the inlet and/or the outlet and/or the suctioning channel.

The suctioning channel system is connectable with a suctioning pump. The suctioning pump preferably comprises at least one of the following features:
 The suctioning pump is configured to continuously or intermittently operate.
 The suctioning pump is configured to generate and maintain a negative pressure of −1 to −760 mmHg, preferably −10 mmHg to −500 mmHg (−1.3 kPa to −66.6 kPa), more preferably −25 mmHg to −200 mmHg (−3.3 kPa to −26.6 kPa) as compared to ambient pressure (760 mmHg or 101.3 kPa at sea level).
 The suctioning pump is a vacuum pump (commercially available e.g. from Acelity (www.acelity.com/products/acti-vac-therapy-system) or other manufacturers.

The suctioning channel system comprises at least one stopper for preventing the membrane to be sucked into an inlet of the suctioning channel system, wherein the stopper is formed as a protrusion on the dental splint between the membrane and the inlet of the suctioning channel system.

The suctioning channel system comprises a pressure monitoring and control system.

According to yet another preferred embodiment of the invention, the device comprises a lining. The lining preferably comprises at least one of the following features:
 The lining is provided at portions of the device that are configured to come into contact with the gingiva and/or mucosa of the patient.
 The lining is formed from an air-impermeable material.
 The lining is formed from an elastically deformable (cushioning) material.
 The lining does not surround, partially or fully surrounds the aperture, preferably on the inside of the dental splint.
 The lining consists of a different material as compared to the material of the dental splint, preferably a softer material.
 The lining is attached to and/or covers a part of or the entire inside and/or outside of the dental splint.
 The lining is attached to and/or covers a part of or the entire inner arc and/or the outer arc of the dental splint.
 The lining is attached to and/or covers a part of or the entire inner edge and/or the outer edge of the dental splint.
 The lining is attached to and/or covers one end or both ends of the dental splint.
 The lining has a thickness in a range from 0.1 to 5.0 mm, preferably 0.5 to 4.0 mm, more preferably 1.0 to 3.0 mm.
 The lining is formed from an autopolymerizing and/or cold-curing and/or A-silicone-based and/or permanently soft relining material.
 The lining is formed from Ufi Gel®, preferably Ufi Gel® SC (commercially available from VOCO GmbH, Cuxhaven, Germany; www.voco.com/en). In case of the intraoral device being fabricated by means of 3D-printing technology the relining material consists of any printable soft material suitable to provide sufficient air-tight sealing.
 The lining is attached to the dental splint by means of adhesive, preferably adhesive liquid.
 The lining is formed as an integral part of the dental splint, preferably by 3D-printing technology.

According to yet another preferred embodiment of the invention, the device comprises a purging channel system. The purging channel system preferably comprises at least one of the following features:
 The purging channel system is configured to supply fluid, preferably a purging fluid and/or antiseptics and/or antibiotics and/or analgesics, to the wound treatment area.
 The purging channel system comprises an inlet located outside the dental splint and/or provided on the outside of the dental splint. The inlet may be partially or fully formed and/or defined by the material of the dental splint. The inlet may be connectable to a purging device.
 The purging channel system comprises an outlet. The outlet may comprise at least one of the following features:
  The outlet is located inside the dental splint and/or provided on the inside of the dental splint.
  The outlet is partially or fully formed and/or defined by the material of the dental splint.
  The outlet has at least one orifice. The at least one orifice may converge from an upstream side towards a downstream side thereof. The orifice may be adjacent to the aperture and/or an axis of the orifice may be aligned with a center of the aperture and/or a center of the wound treatment area.

A plurality of orifices may be arranged along and/or around the aperture, preferably equally spaced, more preferably along a part or the entire circumference of the aperture.

The outlet of the purging channel system is arranged at the opposite side of the aperture and/or of the wound treatment area as compared to the inlet of the suctioning channel system.

The outlet is located between the elastic membrane and a lining.

The purging channel system comprises at least one purging channel. The purging channel may comprise at least one of the following features:

The purging channel connects the inlet and the outlet of the purging channel system.

The purging channel has at least one linear portion.

The purging channel has at least one branched portion.

The purging channel has at least one circular portion.

The purging channel partially or fully extends within the dental splint and/or is at least partially or fully formed and/or defined by the material of the dental splint.

The purging channel has a diameter of 0.1 to 5 mm, preferably 0.5 to 4 mm, more preferable in a range from 1 to 3 mm.

The purging channel system comprises at least one tube. The tube may be embedded in the dental splint and/or the elastic membrane and/or the lining. The tube may penetrate the dental splint and/or the elastic membrane and/or the lining. The tube may extend beyond the inside and/or beyond the outside of the dental splint. The tube may partially or fully form and/or define the inlet and/or the outlet and/or the purging channel.

The above object of the invention is also solved by a method for manufacturing an intraoral suctioning device, preferably an intraoral suctioning device according to one of the preceding claims, by preparing a dental splint comprising at least one aperture that is sealed with an elastic membrane so as to define a wound treatment area on the inside of the dental splint, and comprising a suctioning channel system for evacuating the wound treatment area and/or a purging channel system (8) for supplying a purging fluid to the wound treatment area (5).

More specifically, the method may comprise the following steps:

Step A: Preparing a dental splint.

Step B: Forming at least one aperture in the dental splint.

Step C: Sealing the aperture with an elastic membrane so as to define a wound treatment area on the inside of the dental splint.

Step D: Providing the device with a suctioning channel system for evacuating the wound treatment area.

Step E: Providing the device with a purging channel system for supplying a purging fluid to the wound treatment area.

The steps can be carried out in the order as indicated or any other possible order. In case of manufacturing the intraoral suctioning device by 3D-printing technology the above listed steps (A-E) will be carried out in one sequence during the 3D-printing procedure.

The intraoral suctioning device resulting from this manufacturing method (including or not 3D-printing procedures) may comprise at least one of the features of the intraoral suctioning device according to the embodiments disclosed herein.

A method for the intraoral negative pressure wound treatment using the device according to one of the preceding embodiments comprises the following steps:

Step X: Covering a wound on the patient's jaw bone with a porous elastic material.

Step Y: Fitting the device to a patient's jaw so that the wound treatment area comprises the wound and is air-tightly sealed by the device.

Step Z1: Applying a negative pressure to the wound treatment area through the suctioning channel system, so that the elastic membrane is elastically deformed due to the pressure difference inside and outside the elastic membrane in order to compress the porous elastic material onto the wound.

Step Z2: Supplying a purging fluid to the wound treatment area through the purging channel system, so that therapeutically active agents can be delivered to the wound area.

Step Z2 is preferably conducted for 24 hours a day or intermittently for at least one day, preferably for one to two weeks. A negative pressure of −1 to −760 mmHg, preferably −10 mmHg to −500 mmHg (−1.3 kPa to −66.6 kPa), more preferably −25 mmHg to −200 mmHg (−3.3 kPa to −26.6 kPa), as compared to ambient pressure (regularly 760 mmHg or 101.3 kPa at sea level) should be maintained in the wound treatment area. For assessment of the intraoral situation and/or cleaning of the device and/or the wound, the intraoral suctioning device may be removed from the patient's jaw, e.g. once a day. Step Z may be interrupted if complications occur. Preferably, the therapeutic negative pressure is continuously maintained and may be increased in several steps, preferably in three steps. In one example, the negative pressure is maintained at a first level of e.g. −75 mmHg for a first period of time, and is increased to a second level of e.g. −100 mmHg for a second period of time, and finally increased to a third level of e.g. −125 mmHg for a third period of time. Alternatively, the negative pressure can also be applied in a variable or intermittent mode of action.

Step Z2 is conducted after step Z1.

Further preferred embodiments of the invention are obtained by combining features disclosed in the description, drawings and claims.

DETAILED DESCRIPTION OF THE PREFERRED EMBODIMENTS

Figure 1:
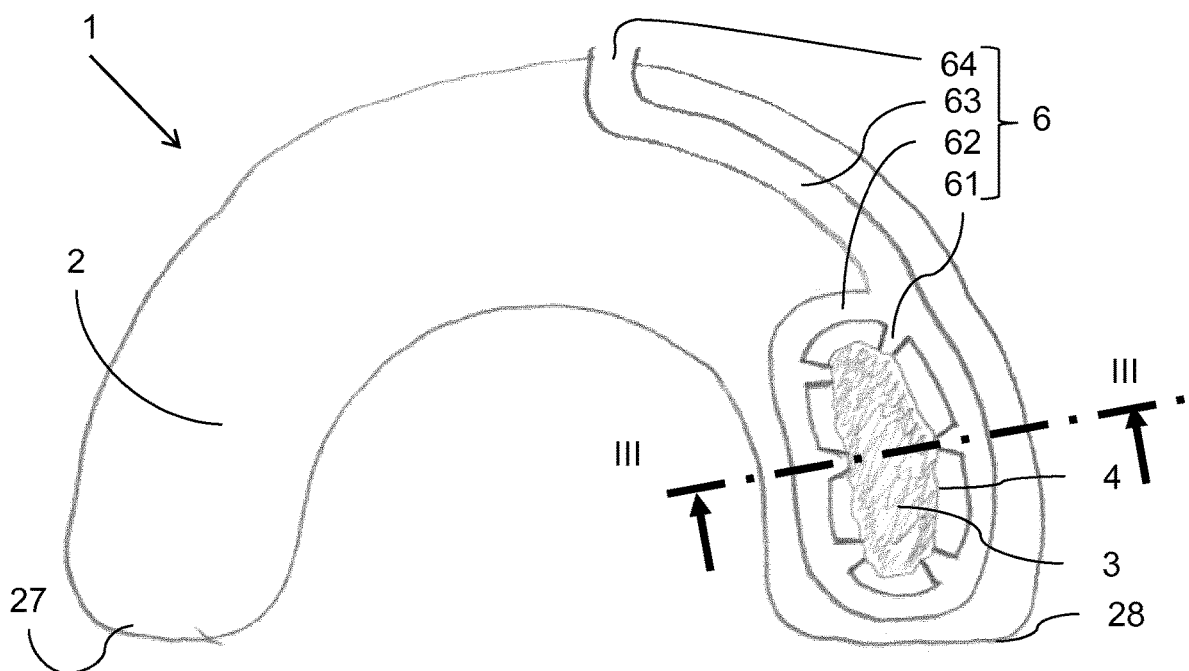
FIG. 1 is a schematic top view of the intraoral suctioning device according to the first embodiment of the invention.

The first embodiment of the intraoral suctioning device 1 according to the present invention as schematically depicted in top view in FIG. 1 is configured to sealingly fit to an upper or lower jaw of a patient and comprises an arc-type or semicircular dental splint 2, and an elastic membrane 3 sealing an aperture 4 corresponding to the outlines of the wound area provided in the dental splint 2, so as to define a wound treatment area 5. A suctioning channel system 6 for removing fluid such as exudates from the wound treatment area 5, is depicted in solid lines for illustrative purposes. In reality, and especially in the case of a 3D-printed intraoral device, the suctioning channel system 6 extends within the dental splint 2 and is not visible from the outside.

The components of the intraoral suctioning device 1 will be described in greater detail below:

The dental splint 2 according to the first embodiment is made from Durasoft® (commercially available from www.scheu-dental.com/en), which is a two-layer pressure-molding plate comprising polyurethane (TPU)/Polyethylen-terephthalat-Glycol Copolyester. In order to perfectly adapt the shape of the dental splint 2 to the specific anatomic conditions of a patient, the dental splint 2 is deep-drawn under vacuum conditions using an ordinary plaster cast model obtained from an alginate impression of a patient's jaw as a template. In case of 3D-printing technology involved in the manufacturing process, the ordinary plaster cast model is scanned, the dental splint 2 is designed on the computer using the digitalized scan data as a model, and the dental splint 2 is then fully or partially printed using appropriate 3D-printable hard and/or soft material(s), wherein the aperture 4 and the elastic membrane 3 covering the same are designed and formed integrally with the dental splint 2 from suitable materials.

As shown in FIG. 1, the dental splint 2 has approximately an arc or semicircular shape as seen in top view that is configured to cover all teeth 11 to 18 and 21 to 28 (if present, or e.g. 11 to 17 and 21 to 27) in tooth quadrants 1 (right) and 2 (left) of the upper jaw, or teeth 31 to 38 and 41 to 48 (if present, or e.g. 31 to 37 and 41 to 47) in tooth quadrants 3 (left) and 4 (right) of the lower jaw according to the FDI tooth scheme (ISO 3950 notation). In case of missing teeth, the dental splint 2 is to cover the corresponding area(s) of the edentulous upper or lower jaw bone.

Figure 3:
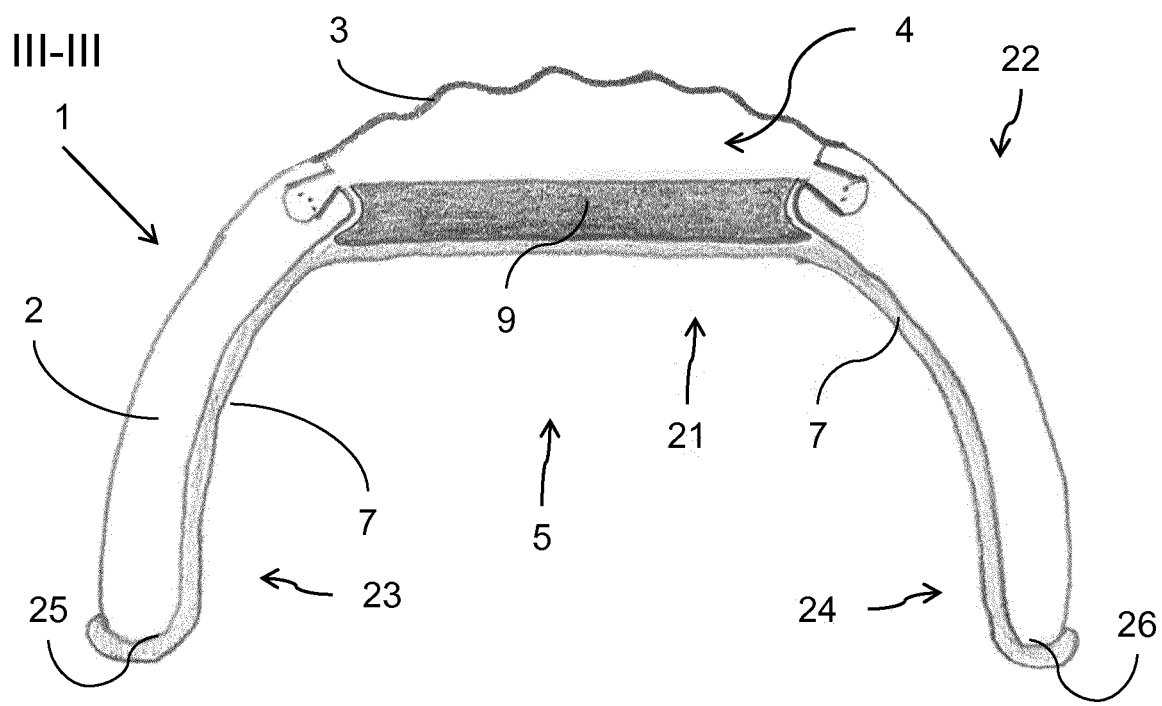
FIG. 3 is a schematic sectional view along line III-III of the intraoral suctioning device as depicted in FIG. 1 before disruption of an obturator plug.
Figure 4:
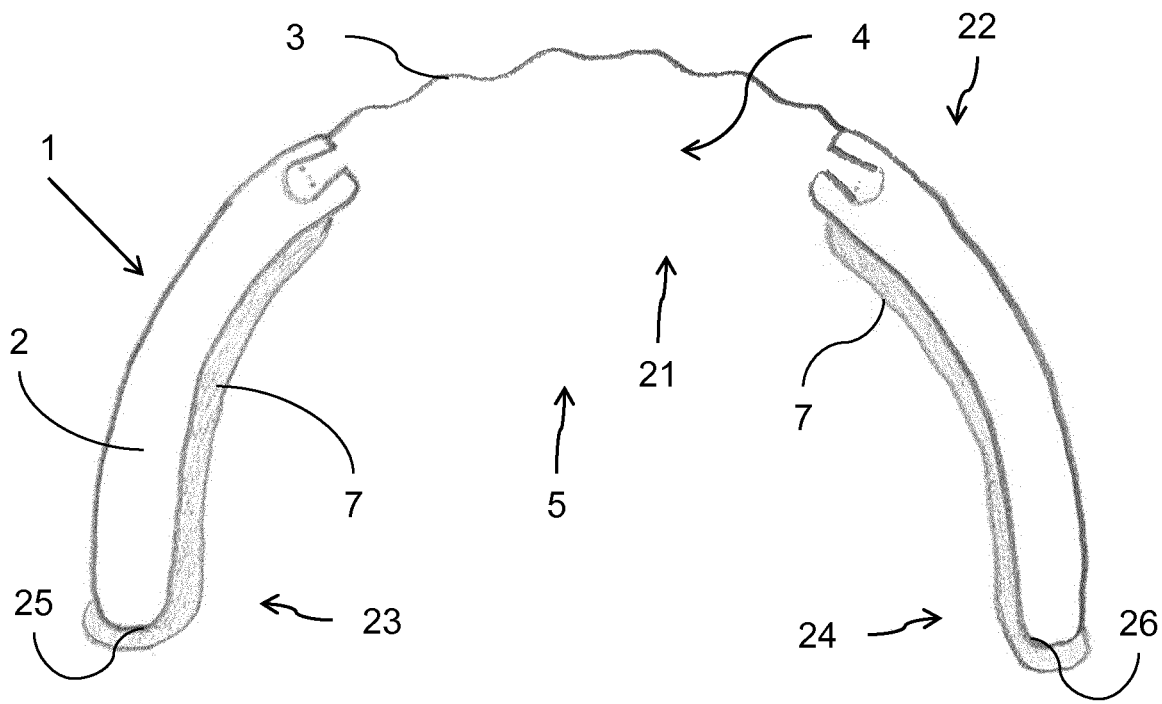
FIG. 4 is a schematic sectional view along line III-III of the intraoral suctioning device as depicted in FIG. 1 after disruption of the obturator plug.

As seen in FIG. 3, the inside 21 of the dental splint 2 is concavely-shaped in cross-section (line III-III of FIG. 1) along the entire length of the dental splint 2, whereas the outside 22 is convexly-shaped in cross-section.

The ends 27, 28 of the dental splint 2 are rounded to increase wearing comfort.

The aperture 4, formed as a through hole extending along a linear axis from the inside 21 to the outside 22 of the dental splint 2, is provided in the dental splint 2, approximately corresponding to teeth 16 to 17 in tooth quadrant 1 (right) or teeth 26 to 27 in tooth quadrant 2 (left) if the dental splint 2 is for the upper jaw, or teeth 36 to 37 in tooth quadrant 3 (left) or teeth 46 to 47 in tooth quadrant 4 (right) if the dental splint 2 is for the lower jaw according to the FDI tooth scheme (ISO 3950 notation). It goes without saying that the aperture 4 may instead be provided in a different portion of the dental splint 2. Alternatively, at least one additional aperture 4 may be provided in a different portion of the dental splint 2. The form and/or location of the aperture 4 as depicted in the drawings are arbitrarily selected and chosen for illustrative purposes only. The aperture 4 can be formed by material removal from the dental splint 2 having a shape adapted to the patient's wound area. In case of a 3D-printed splint, the aperture is accounted for from the outset and, hence, left free during the 3D-printing procedure.

The patch-like elastic membrane 3 is made from an air-impermeable silicone based permanently soft relining material, such as Ufi Gel® SC/P (commercially available from VOCO GmbH; www.voco.com/en). The shape of the elastic membrane 3 is adapted to the shape of the aperture 4 and attached to the inside and/or outside 22 or an edge of the dental splint 2, so as to fully cover and air-tightly seal the aperture 4. The outside of the elastic membrane 3 is exposed to ambient pressure and the elastic membrane 3 is configured to be elastically deformed upon generation of a pressure difference at the inside and the outside of the elastic membrane 3 to enter into the aperture 4. If 3D-printing technology is involved in the manufacturing process, the elastic membrane 3 can be formed integrally with the dental splint 2 by any 3D-printable soft material.

A lining 7 formed from a permanently soft cushioning material, such as Ufi Gel® SC/P (commercially available from VOCO GmbH; www.voco.com/en), is provided at portions that are configured to come into contact with the gingiva and/or mucosa of the patient. More specifically, the lining 7 may fully surround the aperture 4 and may cover the entire inside 21 of the dental splint 2 along the inner and outer arcs 23, 24, the inner and outer edges 25, 26 and both ends 27, 28 thereof, so as to provide maximum patient comfort and adequate sealing. The thickness of the lining is preferably 2 mm. As the lining 7 is elastically deformable and air-impermeable, it achieves proper sealing of the device 1 when fitted to the patient's jaw. The lining 7 can be integrally formed with the elastic membrane 3, if it is made from the same material, or can be used for fixing the elastic membrane 3. It can be made of any 3D-printable soft material in case the splint is produced by 3D-printing technology.

The suctioning channel system 6 comprises an inlet 61 in the form of a plurality of orifices arranged adjacently to the aperture 4 in equal spacing preferably around its entire circumference. Each orifice, i.e. the cross-section thereof, diverges from an upstream side towards a downstream side in order to prevent clogging by debris and/or exudate. The axes of the orifices pass through a center of the aperture 4 to be aligned with a center of the wound treatment area 5. The orifices communicate via branched portions with a circular portion 62 of a suctioning channel, so that removal of air and exudates through the suctioning channel system 6 is possible even in case of clogging of one or several orifices. A linear portion 63 of the suctioning channel having a diameter of approximately 2 mm connects the circular portion 62 of the suctioning channel with an outlet 64 of the suction channel system 6. The inlet 61, the suctioning channel and the outlet 64 of the suction channel system 6 are defined by the material of the dental splint 2 or a plastic tube penetrating the dental splint 2 and/or the elastic membrane 3 and/or the lining 7. In a preferred embodiment, a plastic tube defines a part of the suctioning channel and the outlet 64 of the suction channel system 6, and is connectable with an external tubing of a suctioning pump (not shown). The suctioning channel system 6 is preferably integrally formed with the dental splint 2 if manufactured by means of 3D-printing technology.

Figure 2:
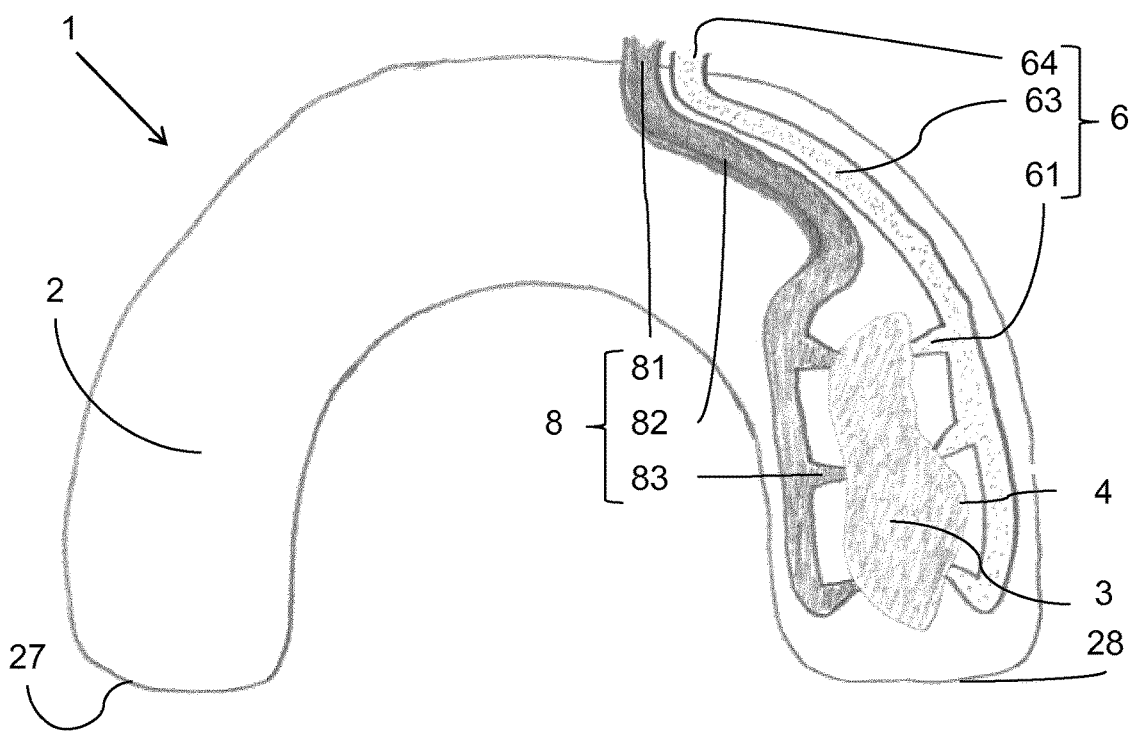
FIG. 2 is a schematic top view of the intraoral suctioning device according to the second embodiment of the invention.

The second embodiment according to FIG. 2 is substantially based on the first embodiment depicted in FIG. 1. Unlike the first embodiment, the second embodiment has a different suctioning channel system 6 and further contains an additional purging channel system 8. The differences between the first and second embodiments will be explained in greater detail below.

In the embodiment of FIG. 2, the plurality of inlet orifices of the suctioning channel system 6 is adjacently arranged to the aperture 4 in equal spacing but only around one half circumference thereof.

The purging channel system 8 is configured to supply a purging fluid from an inlet 81 located on the outside of the intraoral suctioning device 1 through to a purging channel 82 and an outlet 83 to the wound treatment area 5 located on the inside of the intraoral suctioning device 1. The inlet 81 may be defined by a plastic tube embedded into and/or penetrating the dental splint 2 and configured to be connected to a purging device. The whole purging channel system 8 can be integral part of the splint itself if manufactured by means of 3D-printing technology.

The purging channel 82 comprises a plurality of branched portions at a downstream end thereof and connects the inlet 81 with the outlet 83. The outlet 83 has a plurality of orifices ending in the aperture 4 and the wound treatment area 5, respectively. The orifices preferably have a converging cross-sectional shape from an upstream side towards a downstream side thereof. The axes of the orifices 83 are aligned with the centers of the aperture 4 and the wound treatment area 5, respectively. The orifices are equally spaced along the inner or outer half perimeter of the aperture 4. Hence, the outlet 83 of the purging channel system 8 is located at the opposite side of the aperture 4 and the wound treatment area 5, respectively, as compared to the inlet 61 of the suctioning channel system 6. This configuration enables the purging fluid to be smoothly supplied through the purging channel system 8 to the wound treatment area 5 for irrigation in order to entrain and flush exudates and the like from within the wound treatment area 5, and to be subsequently removed from the wound treatment area 5 through the suctioning channel system 6. The purging channel 82 has a diameter of approximately 2 mm and is preferably defined by the material of the dental splint 2. The purging channel 82 may continue outside the dental splint 2 within a purging tube forming the outlet 81 of the purging channel system 8. The purging tube is connectable to a purging device supplying the purging fluid. The whole purging channel system 8 can be integrated in the dental splint 2 itself by means of 3D-printing technology.

As shown in FIG. 3, prior to relining the splint, the aperture 4 is closed by an obturator plug 9. The obturator plug 9 is fixed in position and may be partially or fully covered by the lining 7 on the inner side thereof during the relining procedure, and can thereafter be removed e.g. by cutting with a scalpel from and to the inside 21 of the dental splint 2. The purpose of the obturator plug 9 is to protect the orifices of all inlets 61 and outlets 83 from clogging by the soft lining material when adapting the dental splint 2 to the individual patient's situation.

The intraoral suctioning device 1 according to the present invention can be manufactured by providing a dental splint 2 comprising at least one aperture 4 that is sealed with an elastic membrane 3 so as to define a wound treatment area 5 on the inside of the dental splint 2, and comprising a suctioning channel system 6 for evacuating the wound treatment area 5.

This method may involve the following method steps:

In step A, the dental splint 2 is prepared. Step A can comprise the following sub-steps:

In sub-step A1, an alginate impression is made in the upper or lower jaw of the patient according to the localization of the wound.

In sub-step A2, an ordinary plaster cast model is made for serving as a template for preparing the dental splint 2.

In step A3, the dental splint 2 is formed by 3D-printing after 3D-scanning the plaster cast model, or by deep-drawing a pressure molding material under vacuum conditions on the basis of the plaster cast model.

In step A4, the inside 21 of the dental splint 1, i.e. inner surface that is configured to come into contact with the gingiva or mucosa, is covered with a lining 7 in order to achieve proper sealing and enhance patient comfort. This step may not be required in 3D-printed splints.

In step B, an aperture 4 is formed by removing material from the dental splint 2. Therefore, a piece of variable size—corresponding to the area of the wound—of the dental splint 2 resulting from step A is cut out or left out to provide sufficient room for a (semi-occlusive) compressible porous foam or sponge material to cover the wound. This step may not be required in a 3D-printed dental splint 2.

In step C, the aperture 4 in the dental splint 2 is covered and sealed with a patch-like elastic membrane 3 (e.g. from Ufi Gel®). The elastic membrane 3 is attached to the dental splint 2 in order to extend across the aperture 4 so as to define a wound treatment area 5 at the inside 21 of the dental splint 2. This step may not be required in a 3D-printed dental splint 2.

In step D, a suctioning channel system 6 for evacuating the wound treatment area 5 is formed. This can be achieved by integrating a plastic tube into the dental splint 2 and/or elastic membrane 3 and/or lining 7. The plastic tube serves as a connection between the wound treatment area 5 and an external tubing system of a vacuum pump that is used to generate the required negative pressure. This step may not be required in a 3D-printed dental splint 2.

In step E, a purging channel system 8 for supplying a purging fluid to the wound treatment area 5 is formed. This can be achieved by integrating a plastic tube into the dental splint 2 and/or elastic membrane 3 and/or lining 7. The plastic tube serves as a connection between the wound treatment area 5 and an external tubing system of a delivering device. This step may not be required in a 3D-printed dental splint 2.

The steps can be carried out in the order as indicated or in any other feasible order. If 3D-printing technology is used, the step(s) A4 and/or B and/or C and/or D and/or E as outlined above can be fully or in part integrated into the 3D-print manufacturing process.

Hence, the dental splint 2 forms the mechanical backbone of the intraoral suctioning device 1 according to the present invention that allows a permanent, firm and sealed fit of the device on the patient's jaw. Further components such as the elastic membrane 3, the aperture 4, the suctioning channel system 6, the lining 7 and the purging channel system 8 can be subsequently and/or separately provided on the dental splint 2 so as to avoid mutual interaction between the components. Therefore, the intraoral suctioning device 1 according to the present invention is capable of permanently maintaining the negative pressure in the wound treatment area, so as to improve the wound treatment and regeneration process.

REFERENCE SIGNS LIST

1 Intraoral suctioning device
2 Dental splint
3 Elastic membrane
4 Aperture
5 Wound treatment area
6 Suctioning channel system
7 Lining
8 Purging channel system
9 Obturator plug
21 Inside (of the dental splint)
22 Outside (of the dental splint)
23 Inner arc (of the dental splint)
24 Outer arc (of the dental splint)
25 Inner edge (of the dental splint)

26 Outer edge (of the dental splint)
27 First end (of the dental splint)
28 Second end (of the dental splint)
61 Orifice/Inlet
62 Circular portion
63 Suctioning channel/linear portion
64 Opening/Outlet
81 Opening/Inlet
82 Purging channel (linear portion)
83 Orifice/Outlet

The invention claimed is:

1. Intraoral suctioning device for intraoral negative pressure wound treatment, the device comprising:
 a rigid dental splint;
 an aperture formed in the dental splint;
 an elastic membrane covering the aperture formed in the dental splint so as to define a sealed wound treatment area on an inside of the dental splint; and
 a suctioning channel system for evacuating the wound treatment area,
wherein
 the elastic membrane is elastically deformable upon evacuation of the wound treatment area due to a pressure difference occurring on both sides of the elastic membrane, so that the elastic membrane enters into the aperture; wherein
 the aperture is formed as a through-hole extending from an interior of the dental splint to an exterior of the dental splint.

2. Intraoral suctioning device according to claim 1, wherein the dental splint is a 3D-printed or vacuum-formed dental splint.

3. Intraoral suctioning device according to claim 1, wherein the device comprises:
 a lining, wherein the lining is provided at portions that are configured to come into contact with a gingiva or mucosa of a patient, and/or wherein the lining does not surround, partially or fully surrounds the aperture.

4. Intraoral suctioning device according to claim 3, wherein the lining is made from a same material as the elastic membrane and/or is integrally formed with the elastic membrane and/or fixes the elastic membrane in position, and/or is fully or partially made as a 3D-printed lining.

5. Intraoral suctioning device according to claim 1, wherein the elastic membrane is attached to the dental splint.

6. Intraoral suctioning device according to claim 1, in combination with a porous elastic material that is a foam-type and/or sponge-type material for at least partially filling a wound treatment area, wherein the porous elastic material is configured to be compressed by the elastic membrane upon evacuation of the wound treatment area.

7. Intraoral suctioning device according to claim 1, wherein the suctioning channel system comprises:
 a plurality of orifices arranged along a circumference of the aperture, wherein
 at least one orifice of the plurality of orifices diverges from an upstream end towards a downstream end thereof, wherein each orifice is adjacent to the aperture and/or an axis of each orifice is aligned with a center of the aperture.

8. Intraoral suctioning device according to claim 1, wherein the device comprises:
 a purging channel system for supplying a purging fluid to the wound treatment area wherein the purging channel system includes a plurality of orifices arranged along a circumference of the aperture, wherein at least one orifice of the plurality of orifices converges from an upstream end towards a downstream end thereof, wherein each orifice is adjacent to the aperture and/or an axis of each orifice is aligned with a center of the aperture.

9. Intraoral suctioning device according to claim 1, wherein the dental splint is formed from thermoplastic polyurethane.

10. Intraoral suctioning device according to claim 1, wherein the dental splint is formed from polycarbonate.

11. Intraoral suctioning device according to claim 1, wherein the dental splint is a deep-drawn dental splint based on a cast model of a patient's upper or lower jaw.

12. Intraoral suctioning device for intraoral negative pressure wound treatment, the device comprising:
 a dental splint;
 an aperture formed in the dental splint;
 an elastic membrane for sealing the aperture formed in the dental splint so as to define a sealed wound treatment area on an inside of the dental splint; and
 a suctioning channel system for evacuating the wound treatment area, wherein
 the elastic membrane is elastically deformable upon evacuation of the wound treatment area due to a pressure difference occurring on both sides of the elastic membrane, so that the elastic membrane enters into the aperture; wherein
 the aperture is formed as a through-hole extending from an interior of the dental splint to an exterior of the dental splint,
 a lining, wherein the lining is provided at portions that are configured to come into contact with a gingiva or mucosa of a patient,
 an obturator plug at least partially covered by the lining for closing the aperture prior to a relining procedure and inside of the dental splint prior to the relining of the dental splint.

13. Intraoral suctioning device according to claim 12, wherein the obturator plug is configured to be removable.

14. Intraoral suctioning device according to claim 12, wherein the lining does not surround the aperture.

15. Intraoral suctioning device according to claim 12, wherein the lining partially surrounds the aperture.

16. Intraoral suctioning device according to claim 12, wherein the lining fully surrounds the aperture.

* * * * *